(12) United States Patent
Gaines, Jr.

(10) Patent No.: US 6,524,311 B2
(45) Date of Patent: Feb. 25, 2003

(54) METHOD AND APPARATUS FOR PERFORMING SPINAL PROCEDURES

(76) Inventor: Robert W. Gaines, Jr., 3101 Woodkirk La., Columbia, MO (US) 65203

( * ) Notice: Subject to any disclaimer, the term of this patent is extended or adjusted under 35 U.S.C. 154(b) by 152 days.

(21) Appl. No.: 09/727,658

(22) Filed: Dec. 1, 2000

(65) Prior Publication Data

US 2002/0068940 A1 Jun. 6, 2002

(51) Int. Cl.[7] .............................................. A61B 17/58
(52) U.S. Cl. ............................ 606/61; 606/70; 606/71
(58) Field of Search ........................ 627/17.11; 606/61, 606/70, 71, 72, 73, 75

(56) References Cited

U.S. PATENT DOCUMENTS

| | | |
|---|---|---|
| 4,041,939 A | 8/1977 | Hall |
| 4,047,524 A | 9/1977 | Hall |
| 4,950,269 A | 8/1990 | Gaines, Jr. |
| 5,067,955 A | 11/1991 | Cotrel |
| 5,129,900 A | 7/1992 | Asher et al. |
| 5,147,360 A | 9/1992 | Dubousset |
| 5,152,303 A | 10/1992 | Allen |
| 5,176,680 A | 1/1993 | Vignaud et al. |
| 5,190,543 A | 3/1993 | Schlapfer |
| 5,254,118 A | 10/1993 | Mirkovic |
| 5,257,993 A | 11/1993 | Asher et al. |
| 5,261,911 A | 11/1993 | Carl |
| 5,261,913 A | 11/1993 | Marnay |
| 5,304,179 A | 4/1994 | Wagner |
| 5,352,229 A | 10/1994 | Goble et al. |
| 5,368,594 A | 11/1994 | Martin et al. |
| 5,395,372 A * | 3/1995 | Holt et al. ................... 606/61 |
| 5,437,671 A | 8/1995 | Lozier et al. |
| 5,474,555 A | 12/1995 | Puno et al. |
| 5,496,321 A | 3/1996 | Puno et al. |
| D368,777 S | 4/1996 | Goble et al. |
| D374,286 S | 10/1996 | Goble et al. |
| D374,287 S | 10/1996 | Goble et al. |
| D374,482 S | 10/1996 | Goble et al. |
| D375,791 S | 11/1996 | Goble et al. |
| 5,582,612 A * | 12/1996 | Lin .............................. 606/60 |
| 5,603,714 A | 2/1997 | Kaneda et al. |
| 5,620,443 A * | 4/1997 | Gertzbein et al. ............ 606/61 |
| 5,624,442 A | 4/1997 | Mellinger et al. |
| 5,743,907 A | 4/1998 | Asher et al. |
| 5,980,521 A | 11/1999 | Montague et al. |
| 5,989,250 A | 11/1999 | Wagner et al. |
| 6,080,156 A | 6/2000 | Asher et al. |
| 6,080,193 A | 6/2000 | Hochshuler et al. |
| 6,136,002 A * | 10/2000 | Shih et al. .................... 606/61 |
| 6,299,613 B1 * | 10/2001 | Ogilvie et al. ................ 606/61 |

* cited by examiner

Primary Examiner—Roy Gibson
(74) Attorney, Agent, or Firm—Knoble & Yoshida, LLC

(57) ABSTRACT

A method of performing a surgical spinal fusion procedure to correct an abnormal spinal curvature preferably involves the use of an improved surgical implant spinal staple that has a main body portion, a pair of apertures and a plurality of tine members for fastening and anchoring the staple to a vertebral body. Most advantageously, the spinal staple includes integral structure for permitting direct attachment of a retaining rod, which lowers the profile of the combined staple and attachment mechanism with respect to conventional systems. The spinal fusion procedure further preferably includes a step of sculpting the attachment areas of the vertebral bodies to create recessed areas into which the spinal staples will be positioned and secured. This creates an implant that essentially has no profile with respect to the surrounding areas of the vertebral bodies. The spinal fusion procedure preferably also is performed by completely removing a number of intervertebral discs and then repositioning the spine so as to achieve bone to bone contact between the affected vertebral bodies, which limits interference with adjacent normal tissue following healing. The sum effect is to permit correction of scoliosis over about half the vertebrae fused by conventional techniques with reduced healing time after surgery.

22 Claims, 9 Drawing Sheets

METHOD AND APPARATUS FOR PERFORMING SPINAL PROCEDURES

BACKGROUND OF THE INVENTION

1. Field of the Invention

This invention relates to surgical instrumentation and processes for the anterolateral surgical correction of such conditions as scoliosis, which is also known as curvature of the spine.

2. Description of the Related Technology

Scoliosis in humans may occur as a result of many different causes, including infection by a disease such as polio, paralytic diseases of neuromuscular etiology, or injury to the spinal column. However, the most common cause of scoliosis in first world countries is a genetically determined growth abnormality of the spinal column which most often characteristically causes the curve to develop when the children are passing from late childhood through adolescence. This condition is known as idiopathic scoliosis.

While prevention and bracing can be effective for some children who develop scoliosis, surgical treatment is commonly when employed when the spinal curvature is too pronounced to respond to bracing or when established curves threaten a normal productive, pain free adult life. The standard surgical treatment for scoliosis since the mid-1950's has been an "instrumented spinal fusion," which typically involves the implantation of metal articles such as hooks or screws to the spinal column at each end of the curve. Retaining rods are then attached to the hooks or screws at the ends of the curve. Surgical instruments are then mechanically used to straighten the spinal column (by twisting the spinal column or jacking it up) and the rods are then attached to the hooks or screws and fixed into place to maintain the position of the spinal column in the lengthened, straightened and corrected position. Surgery may be performed using the anterolateral approach, in which correction of the vertebrae is performed from the patient's front or side or the posterior correction method in which correction of the vertebrae is performed from the rear.

To prevent subsequent loosening of the implants and loss of correction of the deformity, a spinal fusion of the instrumented section of the spinal column is virtually always performed at the same time as the instrumentation. This means that bone chips are placed along portions of the spinal column not covered by the implants. These bone chips or grafts induce the vertebrae which were part of the curvature to grow together (fuse) over a period of weeks to months to years. This fusion maintains the correction of the spinal deformity achieved by the application of the instruments (implants).

Current surgical approaches to spinal instrumentation tend to correct the curvature incompletely, and typically instrument and fuse long segments of the spinal column, most usually 7–14 segments. Such an extensive procedure is unavoidably traumatic to the patient and requires a great deal of recovery time, sometimes more than a year.

In addition, current approaches leave behind spinal implants which, because of their size and bulk, commonly cause problems after their implantation. The profile of these implants, which can be defined as their distance of extension beyond the normal vertebral structure of the patient's spine, can interfere with the muscle in the lumbar spine such as the iliopsoas muscle, the nerves of the lumbar plexus and other critical anatomical structure such as ribs, blood vessels, lungs, the liver and the heart. One such approach is depicted in FIG. 1. This approach, which is described in great detail in U.S. Pat. No. 5,603,714, includes a system 10 for fusing a number of vertebral bodies 12 that utilizes a number of staple elements 14 that have tines for penetrating the vertebral body. As may be seen in FIG. 1, each staple element 14 is anchored to a respective vertebral body 12 by a pair of vertebral screws 16, which extend through apertures 18 defined in the staple elements 14 and each of which includes a threaded portion 20 for penetrating the vertebral body and a head portion 22. Each head portion 22 has a channel 24 defined therein for receiving a retaining rod 26. Each head portion 22 further includes a set screw 28 for finally securing the vertebral screw 16 to the retaining rod 26 at the conclusion of the surgical procedure. As may be seen in FIG. 1, the head portions 22 of the vertebral screws 16 extend significantly beyond the circumferential outer surfaces of the vertebral bodies 12. Accordingly, the system may be said to have a relatively high profile.

A need exists for an improved system and method for performing corrective surgery for spinal conditions such as scoliosis that is less traumatic to and facilitates a more rapid recovery for the patient, and that utilizes implants that present fewer postsurgical problems to the surrounding anatomy of the patient.

SUMMARY OF THE INVENTION

Accordingly, it is an object of the invention to provide an improved system and method for performing corrective surgery for spinal conditions such as scoliosis that is less traumatic to and facilitates a more rapid recovery for the patient, and that utilizes implants that present fewer post-surgical problems to the surrounding anatomy of the patient.

In order to achieve the above and other objects of the invention, a surgical implant spinal staple according to a first aspect of the invention includes a main body portion having an inner surface that is constructed and arranged to engage a vertebral body, an outer surface and means for receiving a fastener for the purpose of fastening the spinal staple to a vertebral body; a plurality of tine members extending from the inner surface, the tine members being constructed and arranged to penetrate the vertebral body in order to anchor the spinal staple to the vertebral body; and rod attachment structure for permitting a retaining rod to be attached to the main body portion, the rod attachment structure being integral with the main body portion.

According to a second aspect of the invention, a method of performing a surgical spinal fusion procedure to correct an abnormal spinal curvature includes steps of surgically approaching a patient's spine; completely removing at least one intervertebral disc in an area of abnormal spinal curvature; realigning those vertebral bodies that were adjacent to at least one of the removed disks; compressing said vertebral bodies so as to achieve bone-to-bone apposition therebetween; and completing the spinal fusion procedure so as to secure the vertebral bodies in bone-to bone contact, thereby promoting relatively rapid healing of the fused area.

According to a third aspect of the invention, a method of performing a surgical spinal fusion procedure to correct an abnormal spinal curvature includes steps of surgically approaching a patient's spine; aligning the spine to a desired, corrected position; sculpting at least one of the vertebral bodies so as to form a recessed area; attaching a spinal implant staple within the recessed area, whereby the spinal implant staple will have a lower profile than it would have the recessed area not been sculpted; and securing a retaining rod to the spinal implant staple.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 2:
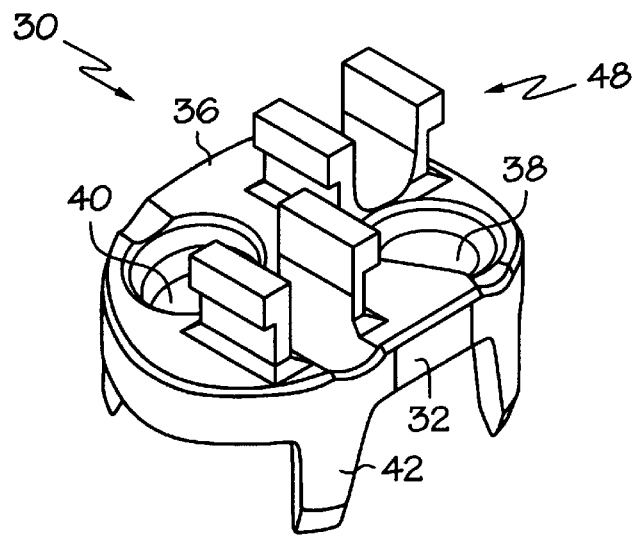
FIG. 2 is a perspective view of an article according to one aspect of the invention, constructed according to a first embodiment.
Figure 3:
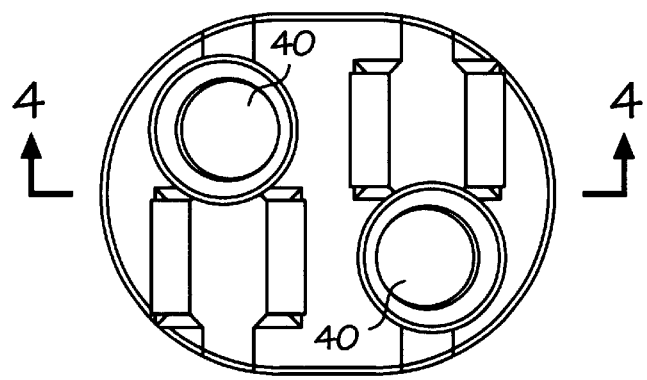
FIG. 3 is a top plan view of the article depicted in FIG. 2.
Figure 4:
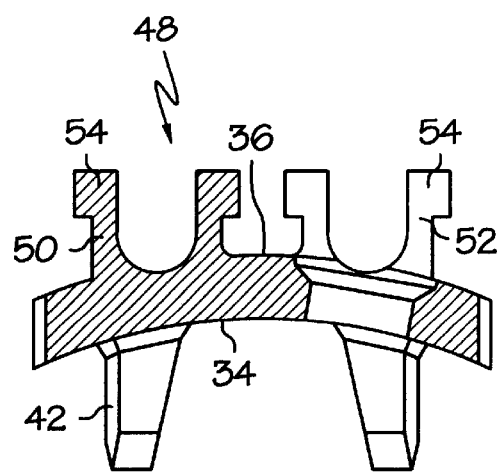
FIG. 4 is a cross-sectional view taken along lines A—A in FIG. 3.
Figure 5:
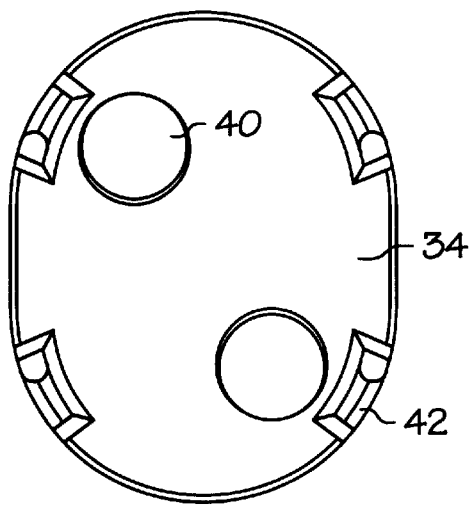
FIG. 5 is a bottom plan view of the article depicted in FIG. 2.

Referring now to the drawings, wherein like reference numerals designate corresponding structure throughout the views, and referring in particular to FIG. 2, one important aspect of the invention involves a surgical implant spinal staple 30 that is designed to have a low profile or no profile at all with respect to a patient's vertebral bodies after corrective spinal surgery. As is shown in FIGS. 2, 3 and 4, surgical implant spinal staple 30 includes a main body portion 32 having an inner surface 34 that is constructed and arranged to engage a vertebral body, as will be discussed in greater detail below. Inner surface 34 is preferably concave, as is been shown in FIG. 4. Staple 30 further includes an outer surface 36 and structure 38 for receiving a fastener for the purpose of fastening the spinal staple 30 to a vertebral body. In the preferred embodiment, structure 38 is embodied as a pair of apertures 40 that are sized to receive a spinal screw, which is not shown.

Figure 6:
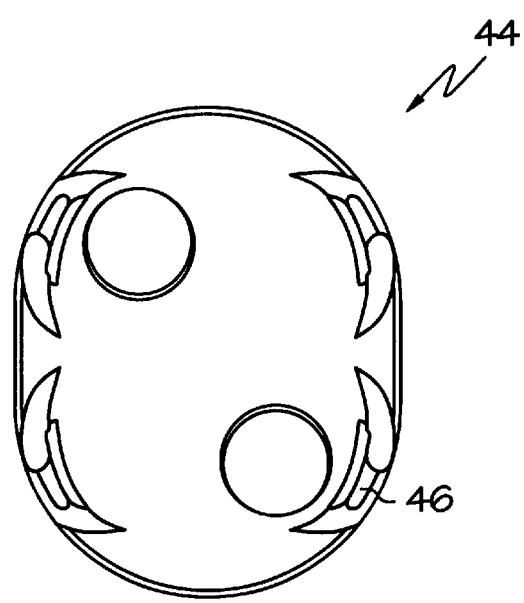
FIG. 6 is a bottom plan view of an article similar to that depicted in FIG. 2, but constructed according to an alternative embodiment of the invention.

Spinal staple 30 also preferably includes a plurality of tine members 42 that extend outwardly from the inner surface 34. The tine members 42 are constructed and arranged to penetrate the vertebral body in order to anchor the spinal staple 30 to the vertebral body. An alternative embodiment shown in FIG. 6 detects a surgical implant spinal staple 44 that is identical in all respects to the staple 30 shown in FIG. 2, with the exception that it has tine members 46, each of which has a central axis, and wherein each tine member is shaped so that when viewed in cross-section transversely to the central axis the tine member is curved so as to have a concave inner surface. This embodiment is preferred when utilizing the surgical procedure involving the sculpting of the vertebral body that is discussed in greater detail below.

Figure 7:
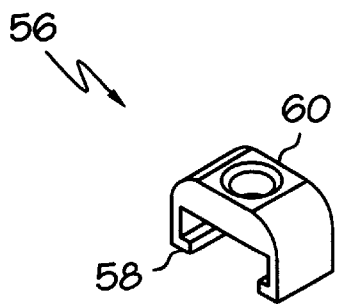
FIG. 7 is a perspective view of a locking cap according to a preferred embodiment of the invention.

Returning to the embodiment of the invention shown in FIGS. 2, 3 and 4, it will be seen that surgical implant spinal staple 30 further includes an integral retaining element attachment structure, which is embodied as a retaining rod attachment structure 48. In the preferred embodiment, retaining rod attachment structure 48 includes a pair of trunnion members 50, 52, each of which includes structure for permitting a retaining rod to be locked into place relative to the trunnion member. In the illustrated embodiment, this locking structure is embodied as a flange 54, which is constructed and arranged to receive a locking cap 56, which is depicted in FIG. 7. As is conventional, locking cap 56 is constructed to define a channel 58 for receiving the flange portion of one of the trunnions 50, 52, and further has a set screw hole 60 defined therein for receiving a set screw, which will be used to lock the staple 30 into position relative to the retaining rod. Alternatively, the retaining element attachment structure could be constructed and arranged to attach to another type of retaining element other than a retaining rod, such as a wire-type retaining system.

Most advantageously, the entire surgical implant spinal staple 30, including the trunnions 50, 52 and the tine members 42, is constructed as a single, unitary member. It may be fabricated from any biocompatible material that has sufficient strength for its intended purpose. The most preferred material is a high-strength biocompatible metallic materials such as titanium.

The surgical implant spinal staple 30, 44 discussed above is quite useful, although not essential, for performing the methods of surgical spinal fusion that are encompassed by the invention. The preferred method of performing a surgical spinal fusion procedure to correct an abnormal spinal curvature according to the invention will now be described with reference to FIGS. 8(a) through 8(g).

Figure 1:
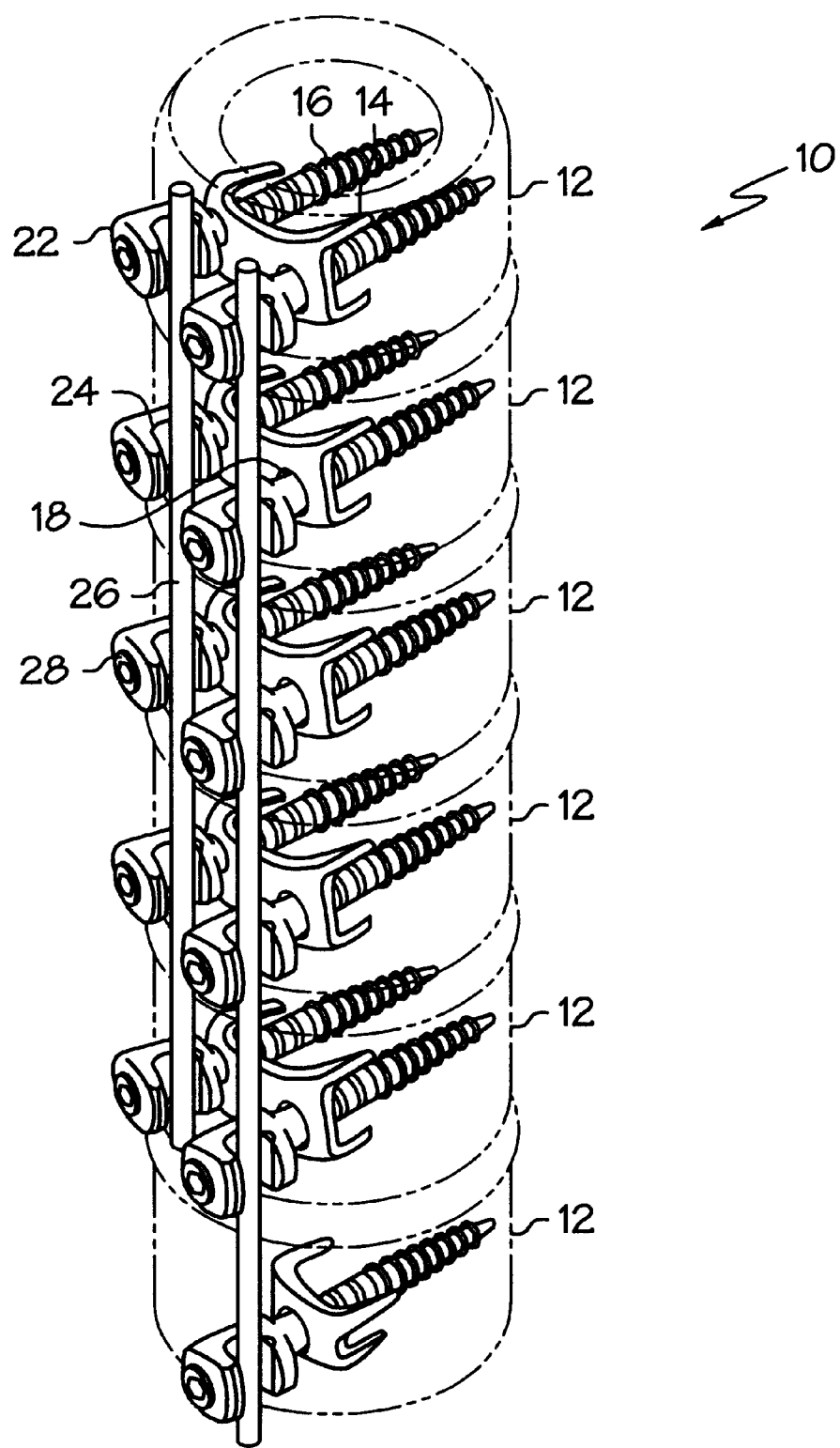
FIG. 1 is a perspective diagrammatical view of one type of a conventional system for surgical correction of spinal curvature.
Figure 8A:
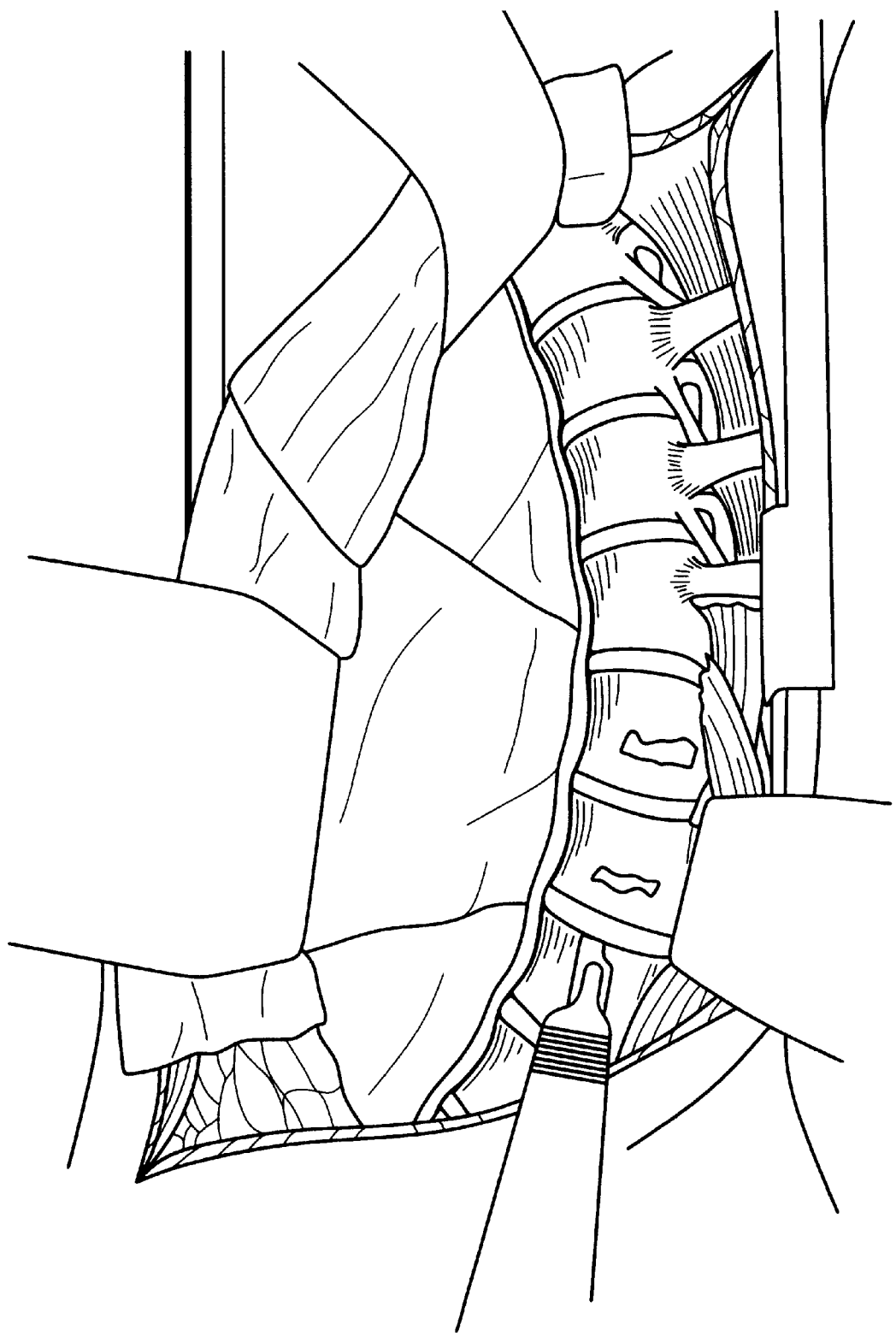
FIGS. 8(a) through 8(g) are diagrammatical drawings depicting performance of a method of performing a surgical spinal fusion procedure according to the preferred embodiment of the invention.
Figure 8B:

As may be seen in FIG. 8(a), the patient is of course anesthetized and is then preferably positioned on his or her side, with the convex side of the spinal curvature facing upwards. The spine is then surgically approached using the anterolateral approach technique, which will involve making an incision in the side of the patient. As may be seen in FIG. 8(b), the affected disks are then completely removed. Because of the effective nature of this procedure to straighten the spine over a relatively few number of vertebrae, fewer vertebrae will need to be fused in order to successfully complete this procedure then would be the case using a conventional procedure of the type that is depicted in FIG. 1. In FIG. 8(b), five discs are shown to be completely removed, indicating that six vertebrae are to be fused. It is anticipated that for most procedures under this method, even fewer vertebrae will need to be fused, although this of course will depend on the particular patient's condition.

Figure 8C:
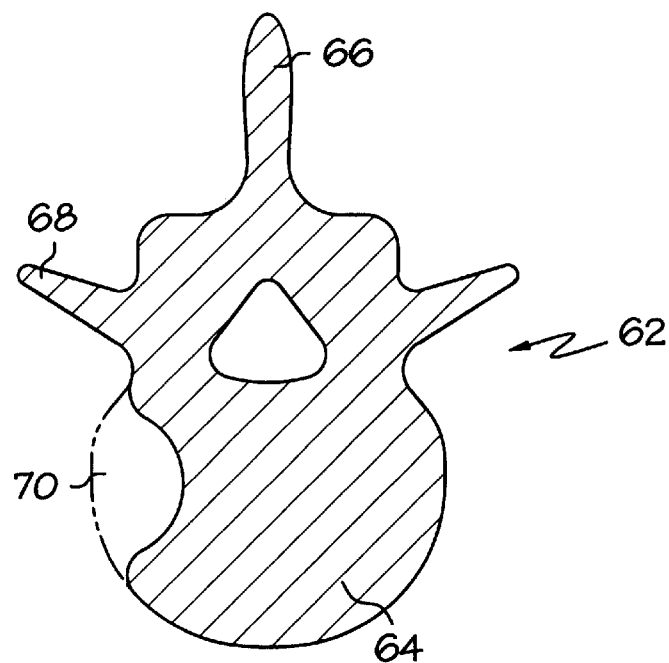
Figure 8D:
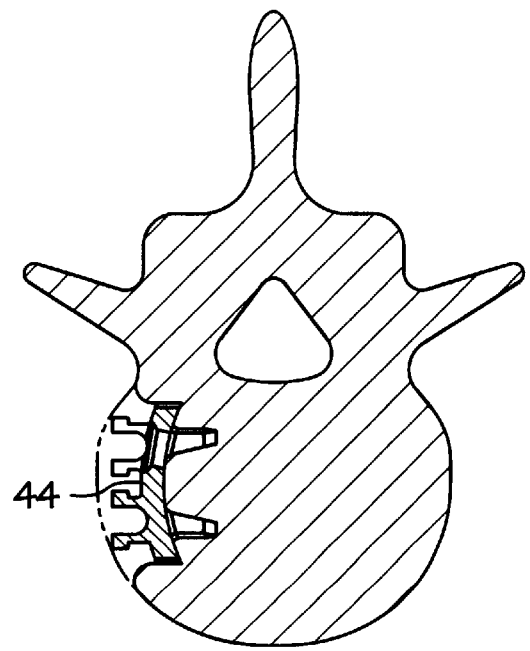

After the discs have been removed, the patient is been repositioned to straighten the spine in rough approximation of the desired final position. FIGS. 8(c) and 8(d) depict a vertebra 62, which includes a vertebral body 64, a spinous process 66, and a transverse process 68. At this point, according to one important aspect of the invention, one side of each of the vertebral bodies to be fused are sculpted so as to form a recessed area 70, which is diagrammatically depicted in FIG. 8(c). As is shown in FIG. 8(d) the spinal implant staple 44 is then inserted into the recessed area 70, and this is preferably performed so that the spinal implant staple 44 will have a lower profile then it would have had the recessed area not been sculpted. Most preferably, this is performed so that the spinal implant staple 44, including the trunnion members, do not extend outwardly beyond the original dimension of the vertebral body 64 as it existed prior to sculpting. As a result, a no profile implant is created.

After the implant staple 44 has been positioned, screws are inserted through the apertures 40 to secure the staple 44 into place. These screws are conventional flat headed surgical screws, and do not have any structure corresponding to the head portions 22 of the screws that are shown in the system 10 that is depicted in FIG. 1. At this point in time, an image intensifier may be used to confirm proper positioning of the implants, and any implants that have been mispositioned will be readjusted.

Figure 8E:
Figure 8F:
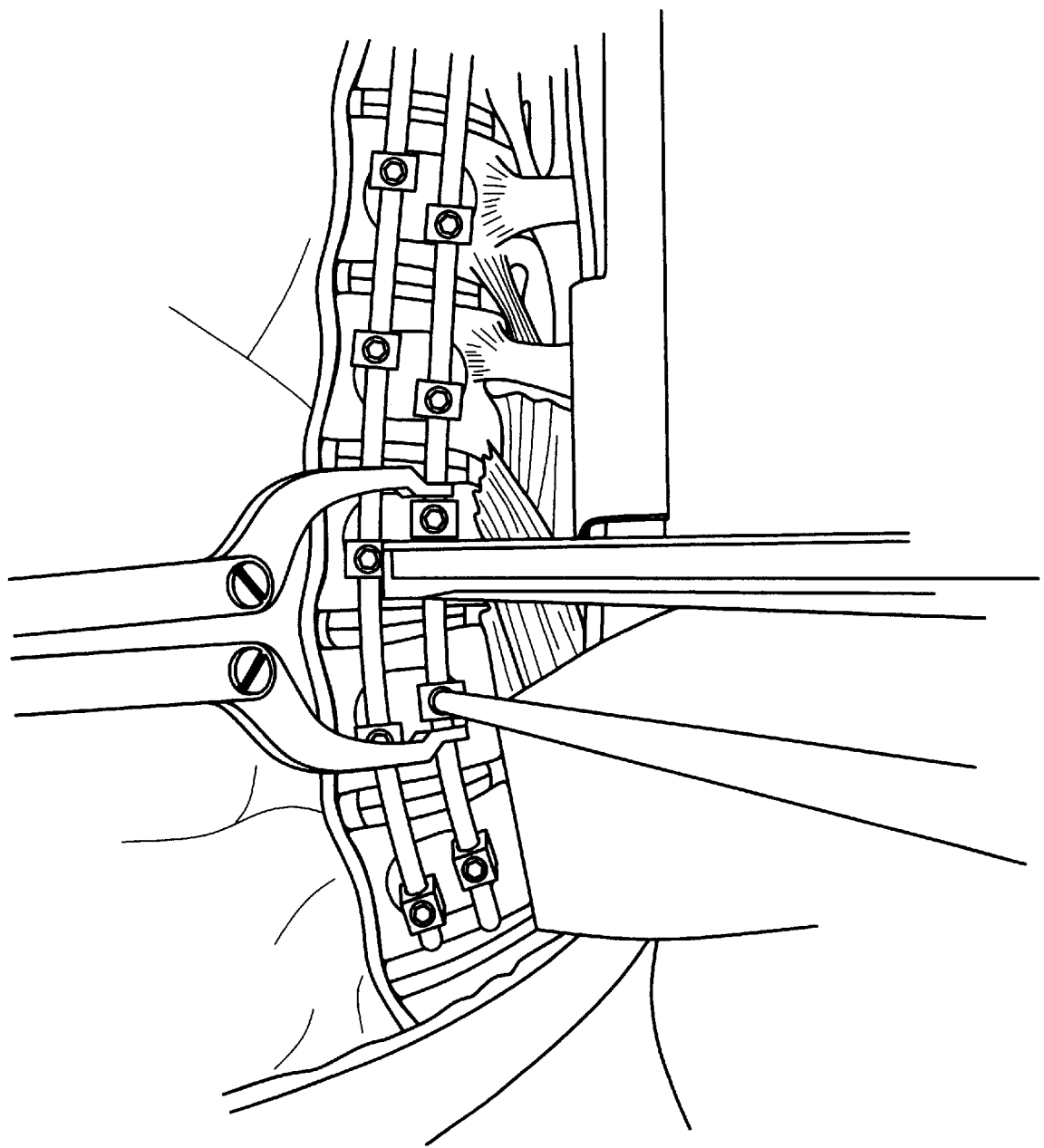

As is conventional, a retaining rod will at this point be shaped and prepared by the surgeon. The retaining rod will be cut to length, and will be bent to an anticipated corrected alignment. As shown in FIG. 8(e), the retaining rod will be dropped into the channels defined by the trunnions of the staple 44, and the locking caps 56 will then be positioned on to the respective trunnion members. The set screws, however, will not be tightened at this point. Once one retaining rod is properly positioned, a compression device as is shown in FIG. 8(f) is used to approximate adjacent vertebrae; this can be done simultaneously for multiple vertebrae or locally for adjacent vertebrae. Because the entire discs have been removed, bone to bone apposition between the vertebrae is possible, and, in fact, is a goal. Previous spinal instrumentation and fusion attempts to straighten a scoliotic spine have achieved incomplete correction and have taken from 4 months to 12 months for full healing to occur. The reason for this delayed healing and incomplete correction, in cases done from the anterolateral approach, has been the tradition of performing incomplete discectomy over the involved discs. No previous approach to surgical correction has ever mentioned complete discectomy as a part of the surgical technique to achieve bone-on-bone apposition through the fusion area. This technique both eliminates structural barriers to full correction and permits the quality of intimate apposition of the vertebrae in the curvature which permits rapid healing (2–3 months) of the operated fusion.

Figure 8G:
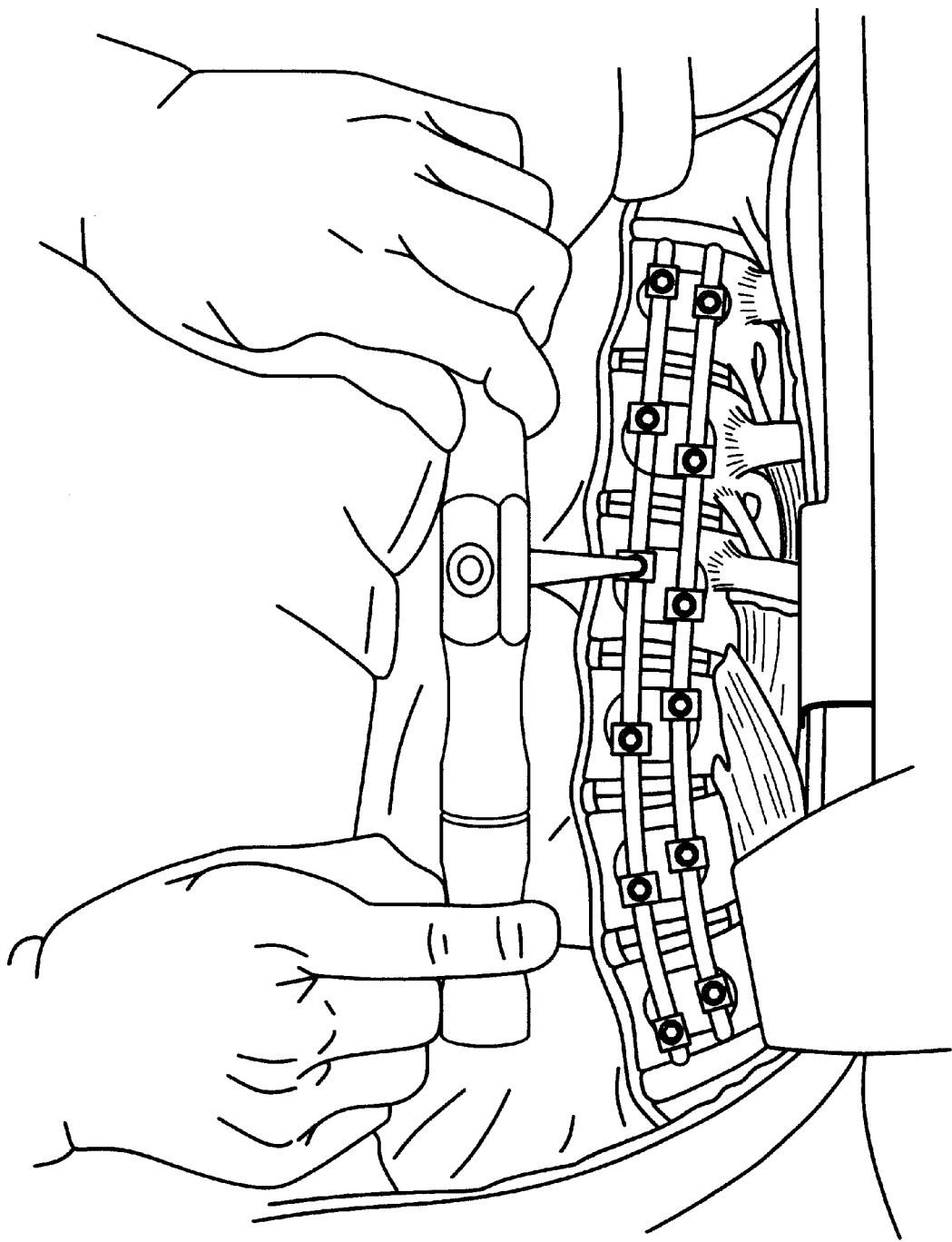

Once bone to bone contact has been achieved, the set screws will be set, as is shown in FIG. 8(g). Position will again be checked by an appropriate imaging device, and any placements that need to be modified will be so modified. The second retaining rod will then be shaped, inserted and secured. The entire area will then be irrigated, an epidural catheter will be inserted for pain control, a chest drain will be inserted, and the wound will be closed. Because of the low-profile of the implants, the minimized number of vertebrae that have been fused and the bone to bone contact of the vertebrae, trauma to the patient is minimized and the patient will be expected to heal very rapidly.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A surgical implant spinal staple, comprising:
    a main body portion having an inner surface that is constructed and arranged to engage a vertebral body, an outer surface and means for receiving a fastener for the purpose of fastening the spinal staple to a vertebral body;
    a plurality of tine members extending from said inner surface, said tine members being constructed and arranged to penetrate the vertebral body in order to anchor the spinal staple to the vertebral body, each of said tine members being shaped so as to have a central axis, and wherein at least one of said tine members is shaped so that when viewed in cross-section transversely to said central axis said tine member is curved so as to have a concave inner surface; and
    retaining element attachment means for permitting a retaining element to be attached to said main body portion, said retaining element attachment means being integral with said main body portion.

2. A surgical implant spinal staple according to claim 1, wherein said inner surface is concave.

3. A surgical implant spinal staple according to claim 1, wherein said means for receiving a fastener for the purpose of fastening the spinal staple to a vertebral body comprises at least one aperture defined in said main body portion for receiving a spinal screw.

4. A spinal implant staple according to claim 3, wherein said means for receiving a fastener comprises two of said apertures.

5. A spinal implant staple according to claim 1, wherein said tine members are unitary with said main body portion.

6. A spinal implant staple according to claim 1, wherein each of said tine members has a central axis, and wherein at least one of said tine members is shaped so that when viewed in cross-section transversely to said central axis said tine member is curved so as to have a concave inner surface.

7. A spinal implant staple according to claim 1, wherein said retaining element attachment means is unitary with said main body portion.

8. A spinal implant staple according to claim 1, wherein said retaining element attachment means comprises at least one trunnion member that defines an interior channel for receiving a retaining rod and for constraining the retaining rod against any movement other then longitudinal movement with respect to the spinal staple.

9. A method of performing a surgical spinal fusion procedure to correct an abnormal spinal curvature, comprising steps of:
    (a) surgically approaching a patient's spine;
    (b) completely removing at least one intervertebral disc in an area of abnormal spinal curvature;
    (c) realigning those vertebral bodies that were adjacent to at least one of the removed disks;
    (d) compressing said vertebral bodies so as to achieve bone-to-bone apposition therebetween; and
    (e) completing the spinal fusion procedure so as to secure said vertebral bodies in bone-to bone contact, thereby promoting relatively rapid healing of the fused area.

10. A method of performing a surgical spinal fusion procedure according to claim 9, wherein step (a) is performed using the anterolateral approach.

11. A method of performing a surgical spinal fusion procedure to correct an abnormal spinal curvature, comprising steps of:
    (a) surgically approaching a patient's spine;
    (b) aligning the spine to a desired, corrected position;
    (c) sculpting at least one of the vertebral bodies so as to form a recessed area;
    (d) attaching a spinal implant staple within the recessed area, whereby the spinal implant staple will have a lower profile than it would have had the recessed area not been sculpted; and
    (e) securing a retaining rod to the spinal implant staple.

12. A method of performing a surgical spinal fusion procedure according to claim 11, wherein steps (c) and (d) are performed so that the spinal implant staple does not extend outwardly beyond the original dimension of the vertebral body prior to sculpting.

13. A method of performing a surgical spinal fusion procedure according to claim 11, wherein step (d) is performed with a spinal implant staple that includes integral attachment structure for the retaining rod.

14. A method of performing a surgical spinal fusion procedure according to claim 11, wherein step (b) is performed by completely removing at least one intervertebral disc in the area of abnormal spinal curvature.

15. A surgical implant spinal staple, comprising:

a main body portion having an inner surface that is constructed and arranged to engage a vertebral body, an outer surface and means for receiving a fastener for the purpose of fastening the spinal staple to a vertebral body;

a plurality of tine members extending from said inner surface, said tine members being constructed and arranged to penetrate the vertebral body in order to anchor the spinal staple to the vertebral body; and retaining element attachment means for permitting a retaining element to be attached to said main body portion, said retaining element attachment means being integral with said main body portion and comprising at least one trunnion member that defines an interior channel for receiving a retaining rod and for constraining the retaining rod against any movement other then longitudinal movement with respect to the spinal staple.

16. A spinal implant staple according to claim 15, wherein said retaining element attachment means further comprises locking means for permitting a retaining rod to be locked into place relative to the trunnion member, thereby precluding any relative movement between the retaining rod and the spinal staple.

17. A spinal implant staple according to claim 16, wherein said locking means comprises structure on said trunnion member for receiving a locking cap.

18. A surgical implant spinal staple, comprising:

a main body portion having an inner surface that is constructed and arranged to engage a vertebral body, and outer surface and means for receiving a fastener for the purpose of fastening the spinal staple to a vertebral body;

a plurality of tine members extending from said inner surface, said tine members being constructed and arranged to penetrate the vertebral body in order to anchor the spinal staple to the vertebral body; and retaining element attachment means for permitting a retaining element to be slidably attached to said main body portion.

19. A surgical implant spinal staple according to claim 18, wherein said retaining element attachment means comprises at least one linear guide surface for slidably receiving a locking cap.

20. A surgical implant spinal staple according to claim 18, further comprising means for securing the locking cap in a locked position relative to said retaining element attachment means.

21. A surgical implant spinal staple according to claim 20, wherein said means for securing the locking cap in a locked position comprises a set screw.

22. A surgical implant spinal staple, comprising:

a main body portion having an inner surface that is constructed and arranged to engage a vertebral body, and outer surface and means for receiving a fastener for the purpose of fastening the spinal staple to a vertebral body;

a plurality of tine members extending from said inner surface, said tine members being constructed and arranged to penetrate the vertebral body in order to anchor the spinal staple to the vertebral body; and retaining element attachment means for permitting a retaining element to be attached to said main body portion, said retaining element attachment means being integral with said main body portion and being constructed and arranged so as to receive a retaining rod and so as to constrain the retaining rod against any movement other than longitudinal movement with respect to the spinal staple.

* * * * *